US005883108A

United States Patent [19]
DeSantis, Jr.

[11] Patent Number: 5,883,108
[45] Date of Patent: Mar. 16, 1999

[54] COMBINATION THERAPY FOR TREATING GLAUCOMA

[75] Inventor: Louis DeSantis, Jr., Fort Worth, Tex.

[73] Assignee: Alcon Laboratories, Inc., Forth Worth, Tex.

[21] Appl. No.: 919,882

[22] Filed: Aug. 28, 1997

Related U.S. Application Data

[63] Continuation of Ser. No. 560,055, Nov. 17, 1995, abandoned.
[51] Int. Cl.$^6$ .................................................. A61K 31/445
[52] U.S. Cl. ........................... 514/317; 514/315; 514/913
[58] Field of Search .................................. 514/315, 317, 514/913

[56] References Cited

U.S. PATENT DOCUMENTS

| | | | |
|---|---|---|---|
| 4,540,408 | 9/1985 | Lloyd | 604/294 |
| 4,599,353 | 7/1986 | Bito | 514/530 |
| 4,690,931 | 9/1987 | Wick, et al. | 514/317 |
| 4,730,013 | 3/1988 | Bondi et al. | 524/42 |
| 4,797,413 | 1/1989 | Baldwin et al. | 514/432 |
| 4,861,760 | 8/1989 | Mazuel et al. | 514/54 |
| 4,876,250 | 10/1989 | Clark | 514/179 |
| 4,911,920 | 3/1990 | Jani et al. | 424/78 |
| 5,093,329 | 3/1992 | Woodward | 514/469 |
| 5,153,192 | 10/1992 | Dean et al. | 514/226.5 |
| 5,212,162 | 5/1993 | Missel et al. | 514/54 |
| 5,240,923 | 8/1993 | Dean et al. | 514/226.5 |
| 5,321,128 | 6/1994 | Stjernschantz et al. | 514/530 |
| 5,371,078 | 12/1994 | Clark et al. | 514/182 |
| 5,378,703 | 1/1995 | Dean et al. | 514/222.8 |
| 5,403,841 | 4/1995 | Lang et al. | 514/226.8 |

FOREIGN PATENT DOCUMENTS

| | | |
|---|---|---|
| 0 215 860 B1 | 8/1989 | European Pat. Off. . |
| 0 299 914 B1 | 4/1993 | European Pat. Off. . |
| 0 728 480 A | 8/1996 | European Pat. Off. . |
| WO 94/13275 | 6/1994 | WIPO . |
| WO 97 02823 A | 1/1997 | WIPO . |

OTHER PUBLICATIONS

Tung, et al., "A quantitative analysis of the effects of excitatory neurotoxins on retinal ganglion cells in the chick," *Visual Neurosci.*, 4:217–223 (1990).

Sisk, et al., "Histological changes in the inner retina of albino rats following intravitreal injection of monosodium L–glutamate,"*Graefe's Arch. Clin. Exp. Ophthalmol.*, 223:250–258 (1985).

Siliprandi, et al., "N–methyl–D–aspartate–induced neurotoxicity in the adult rat retina,"*Visual Neurosci.*, 8:567–573 (1992).

Reif–Lehrer, et al., "Effects of monosodium glutamate on chick embryo retina in culture," *Invest. Rohthalmol. Vis. Sci.*, 14(2):114–124 (1975).

Blanks, J.C., "Effects of monosodium glutamate on the isolated retina of the chick embryo as a function of age: A morphological study," *Exp. Eye Res.*, 32:105–124 (1981).

Olney, et al., "The role of specific ions in glutamate neurotoxicity," *Neurosci. Lett.*, 65:65–71 (1986).

Olney, et al., "The anti–excitotoxic effects of certian anesthetics, analgesics and sedative–hypnotics," *Neurosci. LEtter.*, 68:29–34 (1986).

Price, et al., "CNQX potently and selectively blocks kainate excitotoxicity in the chick embryo retina," *Soc. Neurosci. Abst.*, 14:418 (1988).

David, et al., "Involvement of excitatory neurotransmitters in the damage produced in chick embryo retinas by anoxia and extracellular high potassium," *Exp. Eye Res.*, 46:657–662 (1988).

Caprioli, et al., "Large retinal ganglion cells are more susceptible to excitotoxic and hypoxic injury than small cells," *Invest. Ophthalmol. Vis. Sci.*, 34(Suppl.): 1429 (1993).

Cummins, et al., "Electrophysiology of cultured retinal ganglion cells to investigate basic mechanics of damage," *Glaucoma Update IV*, 59–65 (1991).

Sucher, et al., "N–methyl–D–aspartate antagonists prevent kainate neurotoxicity in rat retinal ganglion cells in vitro," *J. Neurosci.*, 11(4):966–971 (1991).

Massey, S., "Cell types using glutamate as a neurotransmitter in the vertebrate retina," N.N. Osborne and G.J. Chader (Eds.) *Progress in Retinal Research*, Ch. 9, Pergammon Press:Oxford, 399–425 (1990).

Miller, et al., "Excitatory amino acid receptors in the vertebrate retina," *Retinal Transmitters and Modulators: Models for the Brain*, (W.W. Morgan, Ed.) CRC Press, Inc., Boca Raton, II: 123–160 (1985).

Zeevalk, et al., "Action of the anti–ischemic agent ifenprodil on N–methyl–D–aspartate and kainate–mediated excitotoxicity," *Brain Res.*, 522:135–139 (1990).

Ornstein, et al., "Antagonists of the NMDA receptor complx," *DN& P*, 7(1):5–12 (1994).

Lipton, S.A., "Prospects for clinically tolerated NMDA antagonists: open–channel blockers and alternative redox states of nitric oxide," *TINS*, 16(12):527–532 (1993).

*Quest Med.*, 33(2–3):75–85 (1980).

Knepper, et al., "Glycosaminoglycans and Outflow Pathways of the Eye and Brain," *Pediat. Neurosci.*, 12:240–251 (1985–86).

Ingber, et al., "A Possible Mechanism for Inhibition of Angiogenesis by Angiostatic Steroids: Induction of Capillary Basement Membrane Dissolution," *Endocrinology*, 119(4):1768–75 (1986).

Clark, et al., "Angiostatic Steroids as a New Class of IOP Lowering Compounds," *IOVS* 35 (4):1057 (1994).

Rohen, Johannes W., "Why is Intraocular Pressure Elevated in Chronic Simple Glaucoma?" *Ophthalmology*, 90(7):758–765 (1983).

Johnson, et al., "Glaucoma: An Overview," *Mayo Clin. Proc.*, 61:59–67 (1986).

(List continued on next page.)

*Primary Examiner*—Zohreh Fay
*Attorney, Agent, or Firm*—Sally Yeager

[57] ABSTRACT

Methods for treating persons with glaucoma or ocular hypertension with polyamine antagonists and an IOP-lowering compounds are also disclosed.

5 Claims, No Drawings

OTHER PUBLICATIONS

Beal, M.F., "Mechanisms of excitotoxicity in neurologic diseases," *FASEB J.*, 6:3338–3344 (1992).

Choi, D.W., "Excitotoxic cell death," *J. Neurobiol.*, 23:1261–1276 (1992).

Sattayasai, et al., "Morphology of quisqualate–induced neurotoxicity in the chicken retina," *Invest. Ophthalmol. Vis. Sci.*, 28:106–117 (1987).

Patent Abstracts of Japan, 13:208 (C–596), 16 May 1989 and JP 01 026518 A (Eisai Co Ltd), 27 Jan. 1989.

Patent Abstracts of Japan, 15:337 (C–0862), 27 Aug. 1991 and JP 03 128332 A (Eisai Co Ltd), 31 May, 1991.

Physicians' Desk Reference for Ophamology, 16 Edition, 1988. p. 11.

COMBINATION THERAPY FOR TREATING GLAUCOMA

This application is a continuation of application Ser. No. 08/560,055, filed Nov. 17, 1995, now abandoned.

The present invention relates generally to the field of ophthalmology. In particular, the invention relates to the treatment of glaucoma using a combination of a polyamine antagonist to preserve visual field and an intraocular pressure lowering compound.

BACKGROUND OF THE INVENTION

Although the underlying causes of glaucoma are not understood at this time, glaucoma is characterized by damage to the optic nerve, accompanied by a decrease in the normal visual field. One early warning sign of possible glaucomatous visual field loss is elevated intraocular pressure ("IOP"). In fact, glaucoma has historically been treated by medically and/or surgically lowering elevated IOP, for example, by the administration of IOP-lowering agents such as motics, sympathomimetics, beta-blockers, and carbonic anhydrase inhibitors. However, factors other than IOP may play a role in the occurrence of visual field loss. Degeneration of retinal ganglion cells may be related to ischemia or mechanical distortion of the nerve fibers as they exit through the optic nerve head or from pathological perturbations of the retina.

There has been a growing interest in retinal dysfunction as a contributor to the glaucomatous process. Retinal dysfunction, and hence pathology, may be related to ischemia or excitotoxicity. Excitotoxicity is neuronal injury due to excessive excitatory amino acid ("EAA") stimulation. In the inner retina, glutamate is the major EAA that permits the bipolar and amacrine cells to communicate with the ganglion cell. In the central nervous system, excitotoxicity results from hypoxia, ischemia, hypoglycemia or trauma. (See, for example, Beal, M. F., "Mechanisms of excitotoxicity in neurologic diseases," *FASEB J.*, 6:3338–3344 (1992); and Choi, D. W., "Excitotoxic cell death," *J. Neurobiol.*, 23:1261–1276 (1992).) Toxicity to the inner retina has been observed following intravitreal injection of EAAs following application of EAAs to the isolated animal retina or from exogenously applied glutamate to retinal ganglion cells in culture. See generally, Sattayasai, et al., "Morphology of quisqualate-induced neurotoxicity in the chicken retina," *Invest. Ophthalmol. Vis. Sci.*, 28:106–117 (1987); Tung et al., "A quantitative analysis of the effects of excitatory neurotoxins on retinal ganglion cells in the chick", *Visual Neurosci.*, 4:217–223 (1990); Sisk et al., "Histological changes in the inner retina of albino rats following intravitreal injection of monosodium L-glutamate," *Graefe's Arch. Clin. Exp. Ophthalmol.*, 223:250–258 (1985); Siliprandi et al., "N-methyl-D-aspartate-induced neurotoxicity in the adult rat retina," *Visual Neurosci.*, 8:567–573 (1992); Reif-Lehrer et al., "Effects of monosodium glutamate on chick embryo retina in culture," *Invest. Ophthalmol. Vis. Sci.*, 14(2):114–124 (1975); Blanks, J. C., "Effects of monosodium glutamate on the isolated retina of the chick embryo as a function of age: A morphological study," *Exp. Eye Res.*, 32:105–124 (1981); Olney et al., "The role of specific ions in glutamate neurotoxicity," *Neurosci. Lett.*, 65:65–71 (1986); Olney et al., "The anti-excitotoxic effects of certain anesthetics, analgesics and sedative-hypnotics," *Neurosci. Lett* 68:29–34 (1986); Price et al., "CNQX potently and selectively blocks kainate excitotoxicity in the chick embryo retina," *Soc. Neurosci. Abst.*, 14:418 (1988); David et al., "Involvement of excitatory neurotransmitters in the damage produced in chick embryo retinas by anoxia and extracellular high potassium," *Exp. Eye Res.*, 46:657–662 (1988); Caprioli et al., "Large retinal ganglion cells are more susceptible to excitotoxic and hypoxic injury than small cells" *Invest. Ophthalmol. Vis. Sci.*, 34(Suppl):1429 (1993); Cummins et al., "Electrophysiology of cultured retinal ganglion cells to investigate basic mechanics of damage," *Glaucoma Update IV*, 59–65 (1991); and Sucher et al., "N-methyl-D-aspartate antagonists prevent kainate neurotoxicity in rat retinal ganglion cells in vitro," *J. Neurosci.*, 11(4):966–971 (1991).

EAA receptors have been characterized as metabotropic or ionotropic. Activation of a metabotropic receptor affects cellular processes via G-proteins; whereas ionotropic receptors affect the translocation of mono- and divalent cations across the cell membrane. There are at least three ionotropic receptors that have been named for the agonist that preferentially stimulates the receptor. These receptors have been classified as: N-methyl-D-aspartate (NMDA); kainate; and AMPA (2-amino-3-(3-hydroxy-5-methylisoxazol-4-yl) propanoic acid). These EAA receptors are differentially distributed to specific cells in the retina. (See, for example, Massey, S., "Cell types using glutamate as a neurotransmitter in the vertebrate retina," N. N. Osborne and G. J. Chader (Eds.) *Progress in Retinal Research*, Ch. 9, Pergammon Press: Oxford, 399–425 (1990); and Miller et al., "Excitatory amino acid receptors in the vertebrate retina," in *Retinal Transmitters and Modulators: Models for the Brain*, (W. W. Morgan, Ed.) CRC Press, Inc., Boca Raton, II:123–160 (1985).) The localization of such receptors would account for the pathologies associated with glaucoma or inner retinal ischemia. For example, death of the retinal ganglion cell has to a large part been attributed to the NMDA receptor. (See, for example, Sucher et al., "N-methyl-D-aspartate antagonists prevent kainate neurotoxicity in retinal ganglion cells in vitro," *J. Neurosci.*, 11(4):966–971 (1991).). Thus, antagonists of the NMDA receptor are neuroprotective; however, not all antagonists of the diversely distributed EAA receptors are neuroprotective to the inner retina through antagonism of the NMDA receptor, Zeevalk et al., "Action of the anti-ischemic agent ifenprodil on N-methyl-D-aspartate and kainate-mediated excitotoxicity," *Brain Res.*, 522:135–139 (1990)), and many of these EAA antagonists have significant CNS side-effects and are therefore not suitable for treating these degenerative diseases of the eye.

SUMMARY OF THE INVENTION

The present invention is directed to the use of a polyamine antagonist and an IOP controlling agent, dosed separately or in combination for the treatment of persons suffering from glaucoma or ocular hypertension.

DETAILED DESCRIPTION OF THE INVENTION

The present invention involves the use of two types of agents to treat glaucoma and ocular hypertension. One agent is an IOP-lowering agent directed at preventing the damage to retinal ganglion cells brought on by mechanical, circulatory, and other poorly understood factors related to elevated IOP. The second agent is a polyamine antagonist used to prevent further damage to ganglion cells and optic nerve fibers from excitotoxicity.

Eliprodil and other polyamine antagonists are one of four classes of NMDA antagonists. (See, for example, Ornstein et al., "Antagonists of the NMDA receptor complex," *DN&P*, 7(1):5–12 (1994).) The classes include the competitive antagonists which antagonize the glutamate recognition site, non-competitive channel blockers; glycine antagonists and polyamine antagonists, the latter two modulate the glutamate response on the receptor. The glycine and polyamine modulatory sites are distinct. As aforementioned, antagonists of EAA receptors have been used in the CNS to prevent neuronal injury in animal models of ischemia, hypoglycemia and trauma. Pharmacologically, competitive and non-competitive antagonists suffer from their inability to cross the blood-brain barrier or that they produce undesirable (psychotomimetic) side effects. Unlike other NMDA antagonists, the polyamine antagonists such as eliprodil partition across the blood-brain barrier and produce their actions at a modulatory site without side-effects typical of non-competitive antagonists. (See, for example, Lipton, S. A., "Prospects for clinically tolerated NMDA antagonists: open-channel blockers and alternative redox states of nitric oxide," TINS, 16(12): 527–532 (1993).)

Particularly preferred polyamine antagonists are certain 1-phenyl-2-piperidinoalkanol derivatives of formula (1), below:

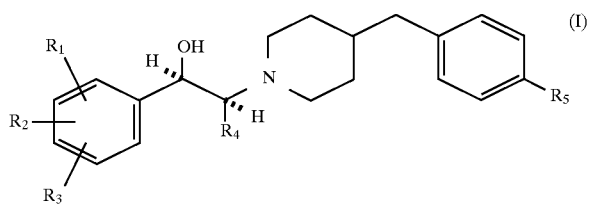

wherein:

$R_1$ represents a hydrogen atom, a halogen atom, a trifluoromethyl group, an alkyl group having from 1 to 4 carbon atoms, a hydroxyl group, an alkoxy group having from 1 to 4 carbon atoms, a benzyloxy group, an alkanoyloxy group having from 1 to 16 carbon atoms or a benzoyloxy group, or, when $R_2$ represents a hydroxyl or methoxy group in the 4-position and $R_3$ represents a hydrogen atom, $R_1$ may also represent a hydroxymethyl group, a carbamoyl group or an alkoxycarbonyl group having from 1 to 4 carbon atoms in the alkoxy part, $R_2$ represents a hydrogen atom, a halogen atom, an alkyl group having from 1 to 4 carbon atoms, a hydroxyl group or an alkoxy group having from 1 to 4 carbon atoms, $R_3$ represents a hydrogen atom or an alkyl group having from 1 to 4 carbon atoms, $R_4$ represents an alkyl group having from 1 to 4 carbon atoms, in which case the compounds are in the (±)-erythro form, or, when $R_3$ represents a hydrogen atom, $R_4$ may also represent a hydrogen atom, and $R_5$ represents a hydrogen atom, a halogen atom, an alkyl group having from 1 to 4 carbon atoms, an alkoxy group having from 1 to 4 carbon atoms or a set of three methoxy groups in the 3-, 4- and 5-positions of the benzyl radical, and pharmaceutically acceptable acid addition salts thereof.

The compounds of formula (I) above are described in U.S. Pat. No. 4,690,931 (Wick et al.); however, there is no mention in that patent of ophthalmic indications for such compounds. Wick et al. also describe methods for synthesizing such compounds. The entire contents of U.S. Pat. No. 4,690,931 are incorporated herein by reference.

The most preferred compounds are: 2-[4-(4-fluorobenzyl)-piperidino]-1-(4-chlorophenyl)-ethanol, also known as eliprodil; 2-(4-benzylpiperidino)-1-(4-hydroxyphenyl)-propanol, also known as ifenprodil; or a pharmaceutically acceptable salt thereof. The structures of eliprodil and ifenprodil are shown below.

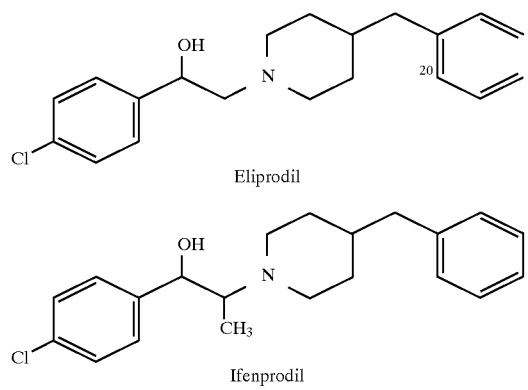

In general, the polyamine antagonists useful in the present invention will be administered orally. Daily dosage of these compounds will range between about 0.1 and about 500 milligrams (mg), preferably between about 5 and about 100 mg. While at the present time there are no effective methods for local administration to the back of the eye for chronic indications, it is contemplated that such methods will be developed. If local chronic administration of these compounds becomes feasible, it is expected that the dosage will range between about 0.1 and about 500 mg, preferably between about 5 and about 100 mg. An aqueous composition will generally contain between about 0.1 and about 10 percent by weight (wt %) of the active, preferably between about 1 and about 5 wt %.

The IOP-lowering agents useful in the present invention, include all presently known IOP-lowering pharmaceuticals, including miotics (e.g., pilocarpine, carbachol and acetylcholinesterase inhibitors); sympathomimetics (e.g., epinephrine, dipivalylepinephrine and para-amino clonidine); beta-blockers (e.g., betaxolol, levobunolol, cartelol, and timolol); prostaglandins and their analogues and derivatives (e.g., F series (such as $PGF_2$), E series (such as $PGE_2$), D series (such as $PGD_2$) and compounds disclosed in U.S. Pat. Nos. 4,599,353; 5,093,329; and 5,321,128, and in European Patent Nos. 0215 860 B1 and 0 299 914 B1; and carbonic anhydrase inhibitors (e.g., acetazolamide, methazolamide, and ethoxzolamide, and compounds disclosed in U.S. Pat. Nos. 5,153,192; 5,240,923; 5,378,703; and 4,797,413). The preferred IOP-lowering agents are: timolol, betaxolol, levobunolol, carteolol, pilocarpine, carbachol, epinephrine, dipivalyl epinephrine, -methyl dipivalylepinephrine, dorzolamide, latanoprost, apraclonidine, and clonidine.

The IOP-lowering agent will be administered in a topical formulation at a concentration of between 0.001 and 5.0 wt %, preferably, 0.01 to 2.5 wt %.

The IOP-lowering compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference.

In addition to the above-described principal ingredients, the IOP-lowering compositions of the present invention may further comprise various formulatory ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, Onamer M® and other agents equally well-known to those skilled in the art. Such preservatives, if utilized, will typically be employed in an amount between about 0.001 and about 1.0 wt %. Examples of suitable agents which may be used to adjust the tonicity or osmolality of the formulations include: sodium chloride, potassium chloride, mannitol, dextrose, glycerin, and propylene glycol. Such agents, if utilized, will typically be employed in an amount between about 0.1 and about 10.0 wt %.

As will be appreciated by those skilled in the art, the compositions may be formulated in various dosage forms suitable for topical ophthalmic delivery, including solutions, suspensions, emulsions, gels, and erodible solid ocular inserts. The compositions are preferably aqueous suspensions or solutions.

The compositions of the present invention may also comprise non-aqueous formulations such as: substantially non-aqueous liquids substantially non-aqueous semi-solid compositions and solid compositions or devices.

The first class, substantially non-aqueous liquids, comprise an IOP-lowering agent and a second agent ("drug combination") dissolved or suspended in one or more of the following: vegetable and mineral oils, such as, liquid petrolatum, corn oil, castor oil, sesame oil, and peanut oil; triglycerides, such as the capric/caprylic triglycerides commonly used in foods and cosmetics; liquid lanolin and lanolin derivatives; and perfluorohydrocarbons.

The second class, semi-solid compositions, comprise an IOP-lowering agent dissolved or suspended in one or more of the following: various types of petrolatum, such as white, yellow, red and so on; lanolin and lanolin derivatives; gelled mineral oil having a hydrocarbon base, such as Plastibase®; petrolatum and ethylene carbonate mixtures; petrolatum in combination with surfactants and polyglycol, such as polyoxyl 40 stearate and polyethylene glycol.

The third class, solid compositions or devices, include non-erodible devices which are inserted into the conjunctival sac of the eye and later removed, such as the Alza-type diffusion or osmotic pressure controlled polymer membranes; and bioerodible polymers which do not have to be removed from the conjunctival sac, such as essentially anhydrous but water soluble polymers and resins (e.g., celluloses, polycarboxylic acids, and so on). Especially preferred are the bioerodible inserts described and detailed in U.S. Pat. No. 4,540,408 (Lloyd) and U.S. Pat. No. 4,730,013 (Bondi et al.), wherein drug combinations of the present invention would be entrained in a non-aqueous matrix consisting essentially of polyvinyl alcohol. The entire contents of these two patents are incorporated herein by reference.

The present invention is also directed to methods of treating persons with glaucoma or ocular hypertension. The polyamine antagonist will be administered systemically and the IOP-lowering compositions described above are applied topically to the affected eye(s) of the patient. The frequency and amount of dosage will be determined by the clinician based on various clinical factors. The methods will typically comprise topical application of one or two drops (or an equivalent amount of a solid or semi-solid dosage form) to the affected eye one to four times per day. The preferred method for treatment is administering eliprodil and betaxolol or timolol.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

I claim:

1. A method for treating a person suffering from glaucoma or ocular hypertension which comprises, administering a polyamine antagonist selected from the group consisting of eliprodil and ifenprodil and an intraocular pressure lowering agent selected from the group consisting of miotics, sympathomimetics, beta-blockers, prostaglandins, and carbonic anhydrase inhibitors.

2. The method of claim 1 wherein the polyamine antagonist is eliprodil.

3. The method of claim 1 wherein the IOP-lowering agent is a beta-blocker.

4. A method for treating a person suffering from glaucoma or ocular hypertension which comprises, administering a pharmaceutically effective amount of eliprodil and betaxolol.

5. A method for treating a person suffering from glaucoma or ocular hypertension which comprises, administering a pharmaceutically effective amount of eliprodil and timolol.

* * * * *